US 6,725,857 B2

(12) United States Patent
Ritsche

(10) Patent No.: US 6,725,857 B2
(45) Date of Patent: Apr. 27, 2004

(54) DISPENSER FOR MEDIA

(75) Inventor: Stefan Ritsche, Eigeltingen (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 421 days.

(21) Appl. No.: 09/803,633

(22) Filed: Mar. 9, 2001

(65) Prior Publication Data

US 2002/0032409 A1 Mar. 14, 2002

(30) Foreign Application Priority Data

Mar. 9, 2000 (DE) .......................... 100 11 120

(51) Int. Cl.⁷ .............................. A61M 15/00
(52) U.S. Cl. ................... 128/200.14; 222/82
(58) Field of Search ................ 222/82; 128/203.15, 128/200.4; 604/62; 239/338

(56) References Cited

U.S. PATENT DOCUMENTS

| 5,469,989 A | * 11/1995 | Graf et al. ..................... 222/82 |
| 5,542,411 A | 8/1996 | Rex |
| 5,964,417 A | * 10/1999 | Amann et al. ............... 239/338 |
| 5,971,951 A | 10/1999 | Ruskewicz |
| 6,179,164 B1 | 1/2001 | Fuchs |

FOREIGN PATENT DOCUMENTS

| DE | 41 06 379 A1 | 9/1991 |
| DE | 197 04 849 | 8/1998 |
| WO | WO 92/00812 | 1/1992 |
| WO | WO 95/27568 | 10/1995 |
| WO | WO 96/09085 | 3/1996 |

* cited by examiner

Primary Examiner—Henry Bennett
Assistant Examiner—Sabrina Dagostino
(74) Attorney, Agent, or Firm—Quarles & Brady LLP

(57) ABSTRACT

The invention relates to a dispenser for dischargeable media, preferably containing at least one active pharmaceutical substance and packed in portioned manner in storage chambers of a storage means, as well as a conveying device for the supply of the storage means.

Figure 1:
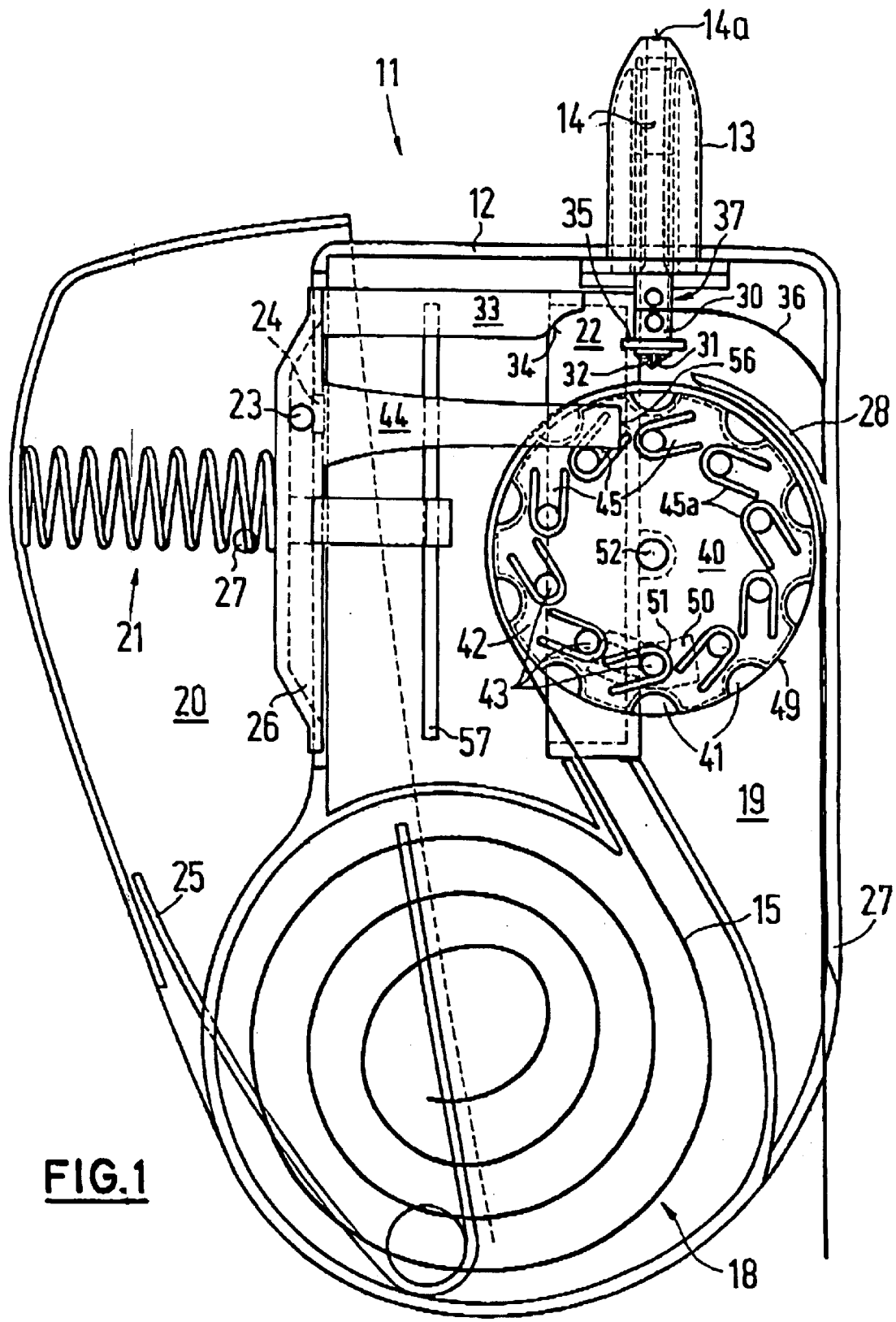

The problem of the invention is to provide a dispenser operable with one hand and able to reliably discharge the medium made available in the storage chambers.

The dispenser has a punch, which can be introduced into the storage chambers. An actuating means is provided according to the invention for the dispenser. An actuation of the actuating means in the sense of performing a discharge process brings about both the positioning of a storage chamber relative to the punch and the discharge of the medium from the storage chamber.

20 Claims, 8 Drawing Sheets

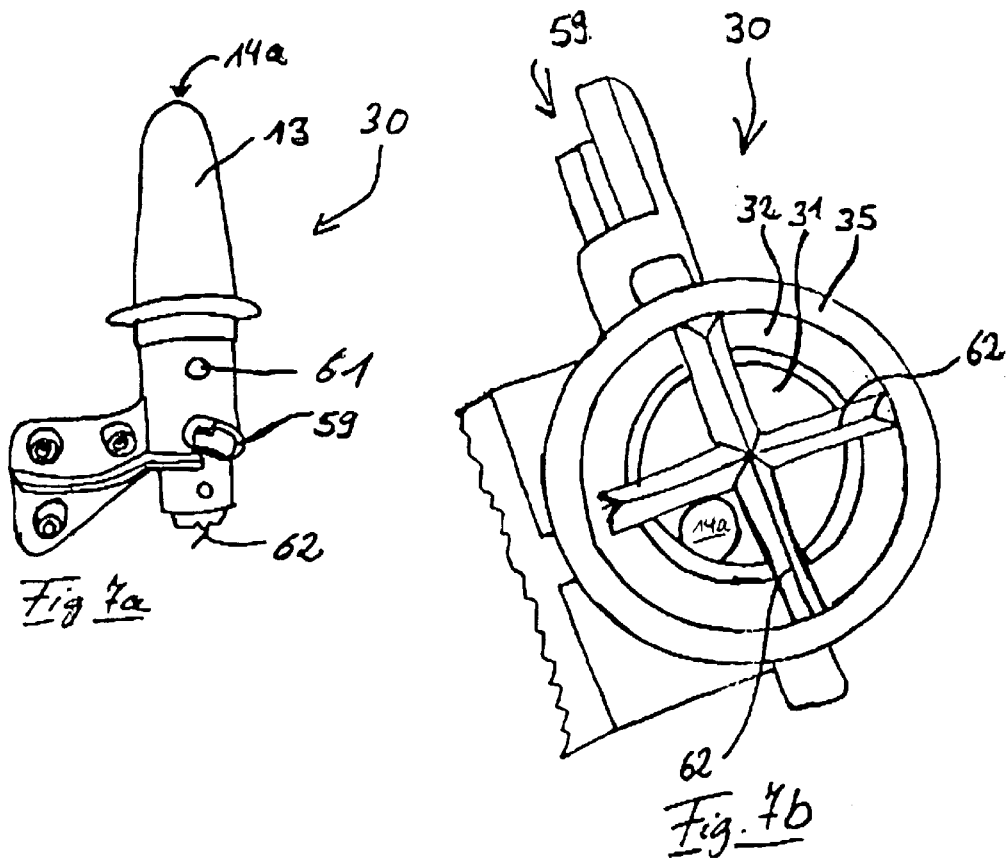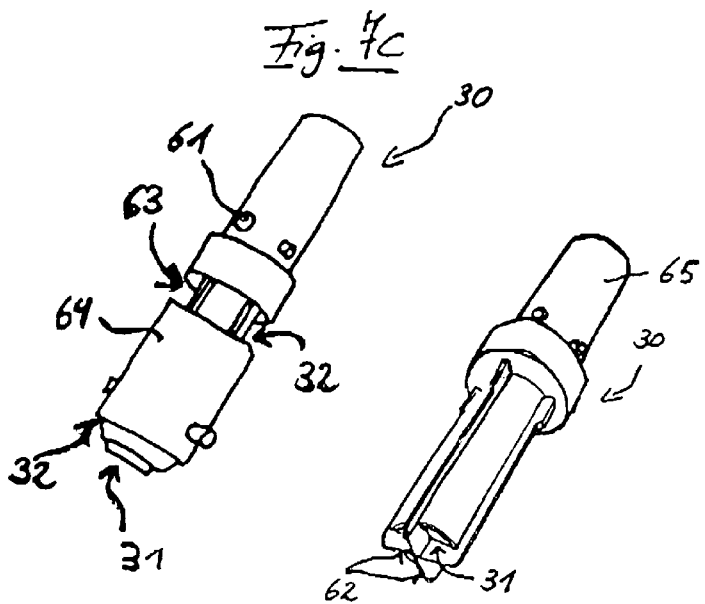

DISPENSER FOR MEDIA

The invention relates to a dispenser for dischargeable media, preferably containing at least one active pharmaceutical substance and packed in portioned manner in the storage chambers of a storage means, as well as a conveying device for the supply of the storage means. The medium can be constituted by all types of flowable media, which can be pulverulent, gaseous and/or liquid. For dosing, storage, hygienic and/or shelf life reasons, it can be advantageous to pack the medium in portioned form in storage chambers, each storage chamber containing a predetermined medium quantity. This quantity preferably corresponds to the quantity to be discharged when applying or administering the medium. The medium can in particular contain an active pharmaceutical substance, e.g. an analgesic or anti-migraine agent, but also other active substances or active substance combinations, which are preferably administered to the patient by nasal application of the medium.

A dispenser according to the prior art can e.g. be gathered from DE 197 04 849 A1. This document describes a dispenser for discharging a medium, which preferably contains at least one active pharmaceutical substance, from a storage chamber of a storage means, the medium being packed in portioned form in the storage chamber. To this end the dispenser has a punch, which is introduceable into the storage chamber.

A disadvantage which occurs in this connection is that the making available of the next storage chamber takes place by an actuation of the dispenser, which differs from the actuation for discharging the medium from the storage chamber. Thus, a two-part actuation of the dispenser is necessary. This is hardly compatible with a one-handed operation of the dispenser.

Moreover, in the case of a dispenser with a revolver or turret-like making available of the storage chambers, it is not ensured that the operator does not accidentally attempt to discharge the medium from an already emptied storage chamber. It is also not ensured that on actuation for making available the following, not yet emptied storage chamber, in actual fact the next available storage chamber is made available, that no storage chamber is skipped and consequently its content is not discharged.

The problem of the invention is to provide a dispenser which can be operated with one hand and which is able to reliably discharge medium kept ready in storage chambers.

On the basis of the dispenser according to the preamble, the invention solves this problem by the features of the independent claims.

A dispenser according to the invention is intended to discharge medium packed in portionwise manner in storage chambers of a storage means and preferably containing at least one active pharmaceutical substance. For this purpose the dispenser has a punch introduceable into the storage chambers. According to the invention an actuating means is provided for the dispenser. An actuation of the actuation means in the sense of performing a discharge process brings about both the positioning of a storage chamber with respect to the punch and the discharge of the medium from the storage chamber.

It is advantageous if in the actuation of the actuating means there is firstly a making available of the next, filled storage chamber, followed by the discharge of the medium from said storage chamber.

It is also advantageous to subdivide the process of discharging the medium from the storage chamber into two parts and during the first part a storage element is pretensioned and during the second actuating part the medium is actually discharged, the storage element being relaxed. Advantageously the storage element is in particular a pump chamber in which, during the first actuating part, an overpressure is built up. It is particularly advantageous if the pump chamber is sealed by an operable valve, which is operated in the opening sense on passing from the first to the second operating part. It is also advantageous if the transition from the first to the second operating part of the medium discharge takes place in path-dependent manner with respect to the actuating path of the actuating means. It is particularly advantageous if the medium is discharged by blowing out by means of the fluid flowing from the pump chamber.

Advantageously the punch has at least one first flow channel for the discharge of the medium from a storage chamber of the storage means.

It is also advantageous if the punch has at least one second flow channel for the supply of fluid from the pump chamber to the storage chamber. It is particularly advantageous if the punch simultaneously constitutes an operating element for the valve sealing the pump chamber. According to a development the punch is constructed in such a way that the second flow channel surrounds in annular manner the first flow channel. As a result of this configuration the fluid on all sides flows uniformly along the outer edge of the storage chamber, meets in the centre at the bottom of the storage chamber and then escapes via the first flow channel whilst entraining the medium to be discharged. This ensures a good discharge.

A conveying device for a storage means with storage chambers in accordance with the present invention is formed by a conveying drum provided on its circumferential surface with receptacles for in each case one storage means.

According to an advantageous development of the invention there is a twist preventer acting on the conveying drum. The twist preventer is constructed in such a way that as a result of its action a receptacle for a storage chamber of the storage means is kept in its aligned position with respect to the punch.

Advantageously a reverse preventer is constructed on the dispenser, which acts on the conveying drum and which is designed in such a way that it allows a rotary movement of the conveying drum in a conveying direction and prevents a rotary movement counter to the conveying direction.

According to an advantageous development the conveying drum is provided on its end face with dogs. Preferably with each receptacle on the circumferential surface of the conveying drum is associated endwise a dog. The actuating means can be constituted by a hook blade, which engages behind the dog and consequently takes over the conveying of the conveying drum by one storage chamber. During the return movement of the hook blade, the latter can be moved past the dogs in axially displaced manner with respect to the conveying drum. This can take place both through a corresponding guide crank for the hook blade and also in that the dogs are elastically fixed to the conveying drum and during the return movement can be displaced from the movement area by the hook blade. It is also advantageous if the actuating means has at least one slide acting on the dogs. According to an advantageous development the slide can be simultaneously constructed as a twist preventer. Advantageously it can also be constructed as a reverse preventer.

It is also advantageous if the slide is so displaceable and guided by means of the actuating means that it is moved along the end face having the dogs on a circular chord and past the conveying drum. It can also be advantageous if the dogs are constructed as preferably cylindrical protuberances projecting axially from the end face and which are positioned on the latter concentrically to the rotation axis of the conveying drum. It is also advantageous if the dogs are positioned on material tongues constructed in the end face. The material tongues are preferably U-shaped and are connected to the end face in the conveying drum rotation direction. The material tongues are constructed in such a way that they can be reversibly bent by the height of the particular protuberance counter to the resulting bending forces towards the interior of the conveying drum.

According to a preferred development of the invention the slide has a substantially beam-like construction. Its longitudinal edge extends in the direction of the circular chord along which the slide is movable with respect to the conveying drum. The end of the slide is directed towards a dog. During an actuating process the end of the slide at least temporarily engages with a dog.

According to another advantageous development of the slide, the latter has a recess. The recess is formed on the side facing the end face of the conveying drum and extends into the vicinity of the longitudinal edge of the slide facing the dogs. The recess serves to receive the dog, which follows the dog which engages with the end of the slide during an actuation.

Preferably the stop face bounding the recess and which is oriented parallel to the end of the slide and located at the rear considered in the slide movement direction is so constructed with respect to its position regarding the terminal edge and dogs that a non-positive connection directed in the conveying direction of the conveying drum can be produced between a dog located in the receptacle and the stop face.

According to another advantageous development the recess has a ramp-like construction on the front side bounding the recess and facing the stop face when considered in the movement direction.

According to another advantageous development the reverse preventer can be at least partly formed in that on the side of the conveying drum diametrically opposite to the slide is provided a reverse preventer, whose preventing action is brought about by frictional connection between a conveying drum-side dog and a casing-fixed contact face, it being possible to pass over the latter in the conveying direction of the conveying drum.

According to an advantageous development of the invention the storage means is constructed in blister strip form, the blister strip having a plurality of storage chambers with dischargeable medium. It is advantageous if the blister strip is in the form of a drum store. The storage means has a uniformly spaced arrangement of storage chambers. Each individual storage chamber is preferably hermetically sealed. The material sealing the storage chamber is at least zonally constructed in such a way that it can be perforated by the punch.

Figure 2:
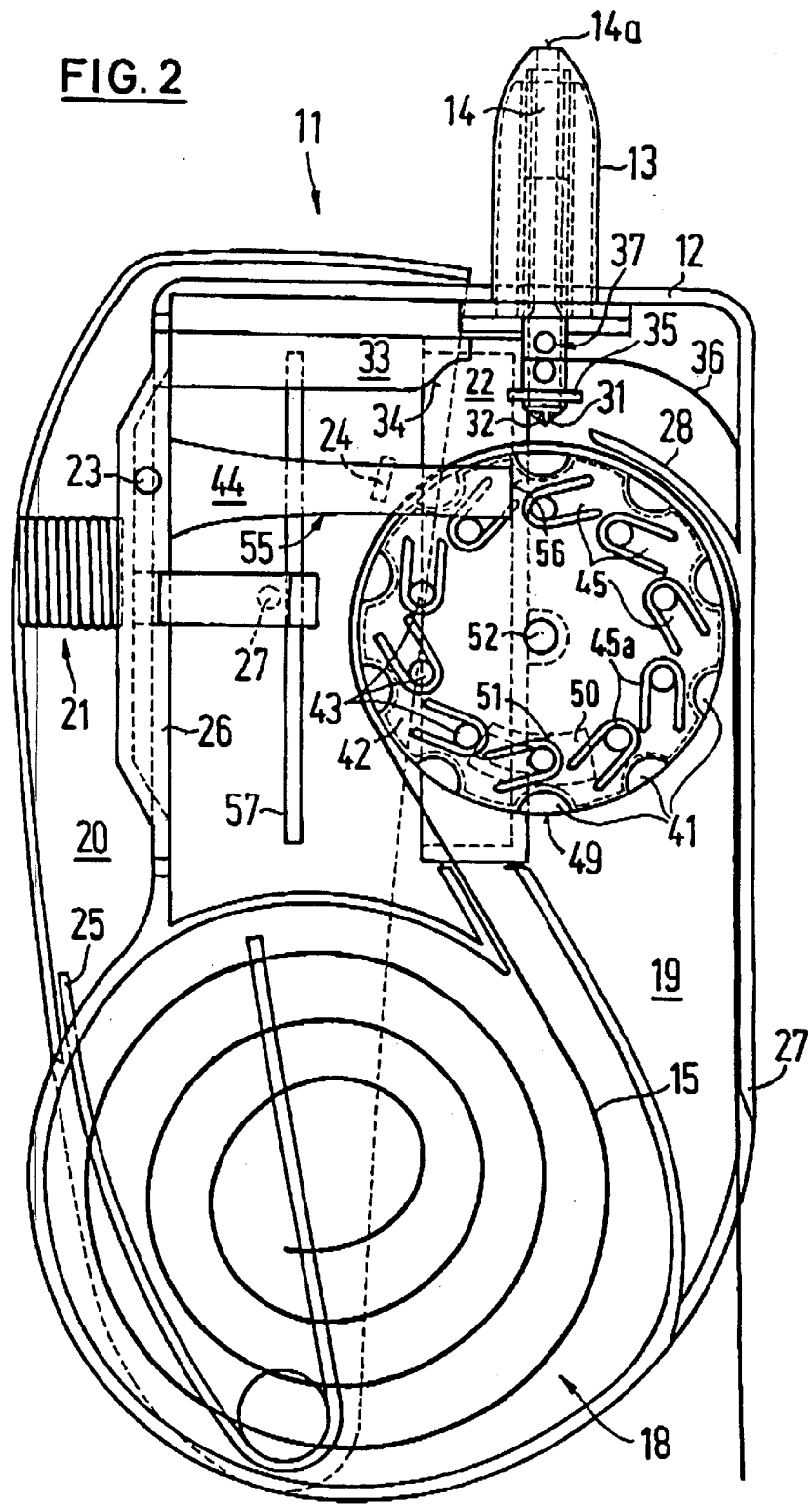
Figure 3:
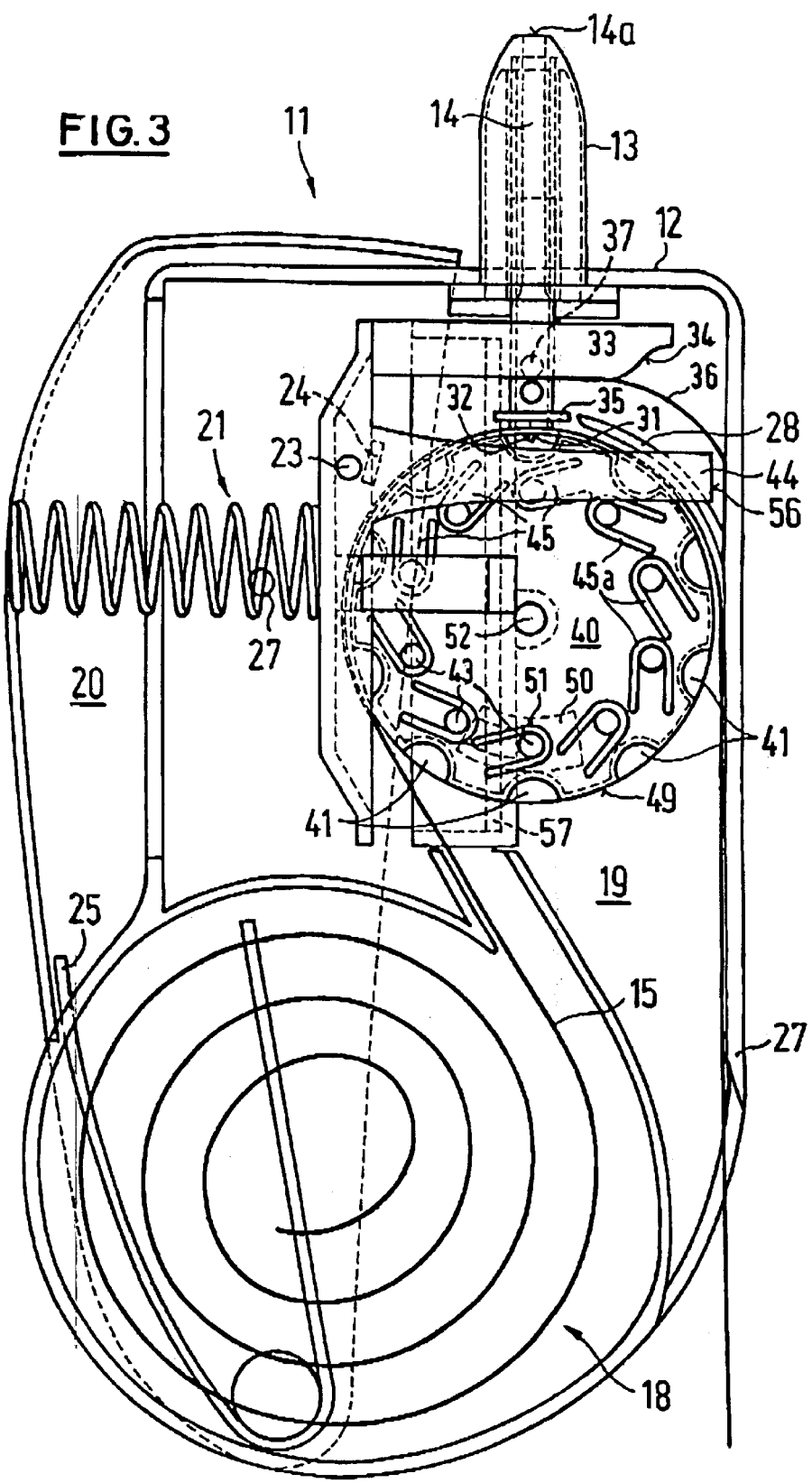

The invention is described in greater detail hereinafter relative to embodiments and the attached drawings, wherein show:

FIGS. 1 to 3 A diagrammatic sectional view of a first embodiment of the invention.

Figure 4:
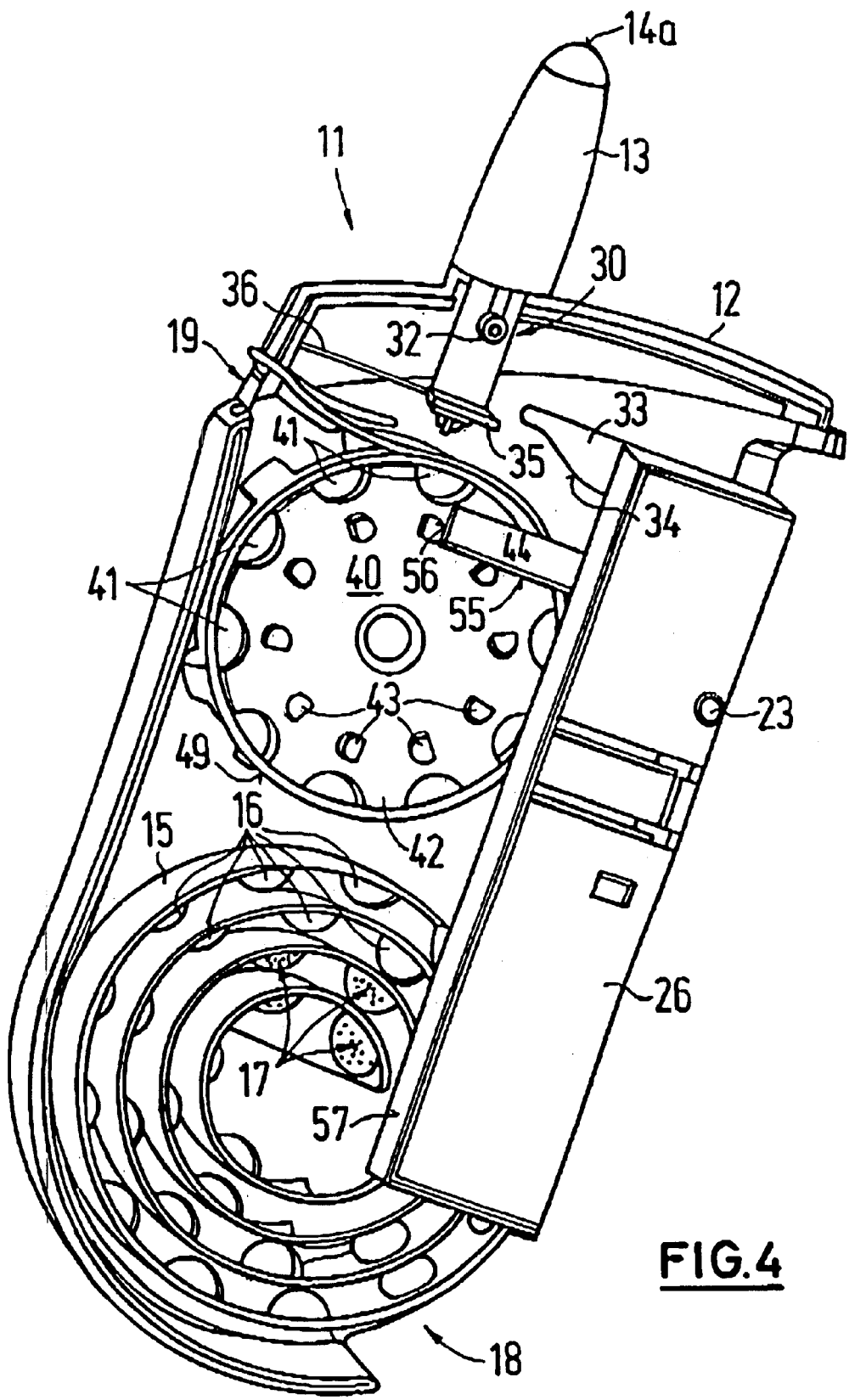

FIG. 4 The diagrammatic representation of a second embodiment in part sectional form.

Figure 5:
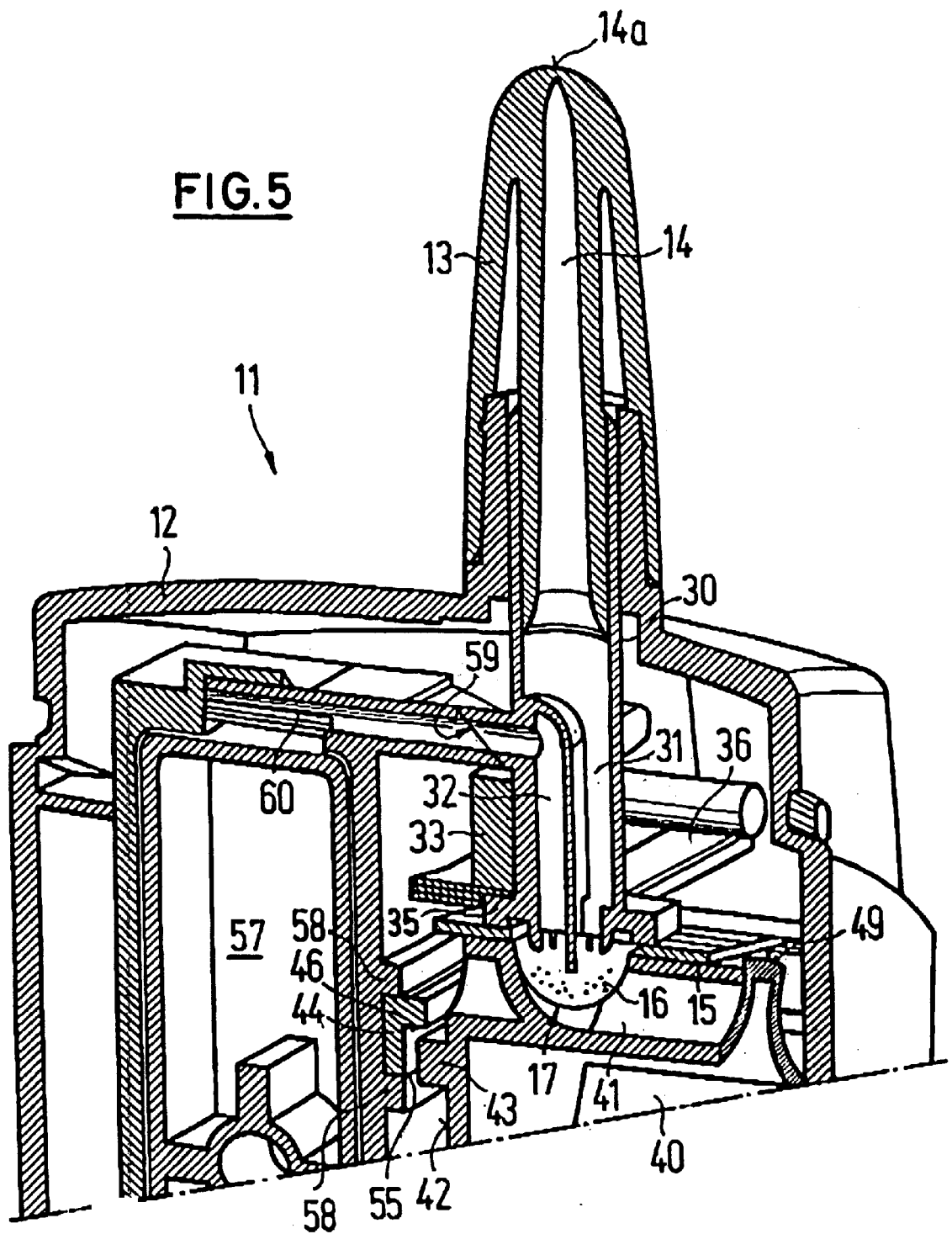

FIG. 5 A diagrammatic cross-sectional representation of a dispenser according to the invention in the vicinity of the discharge channel and the storage chamber from which medium has just been discharged.

Figure 6:
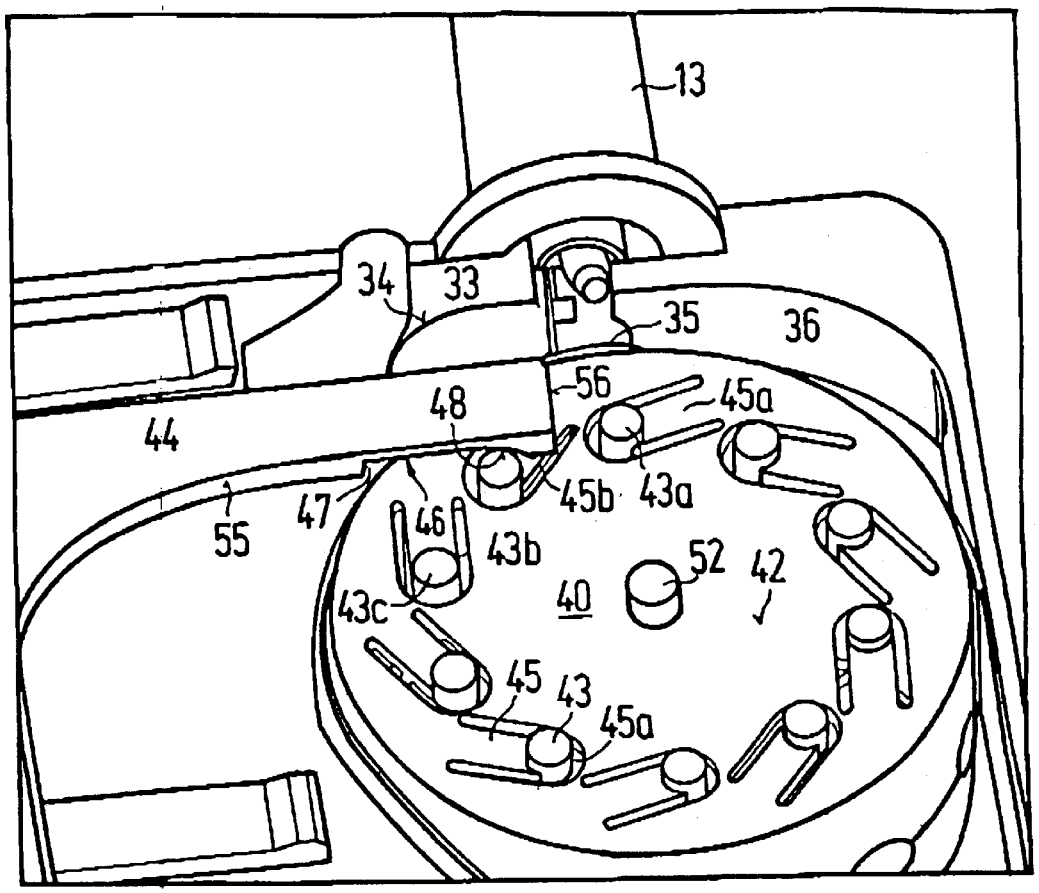

FIG. 6 A larger scale, diagrammatic cross-sectional view of the conveying drum slide.

FIGS. 7a to 7c An alternative construction of the nose adaptor and punch.

Figure 8:
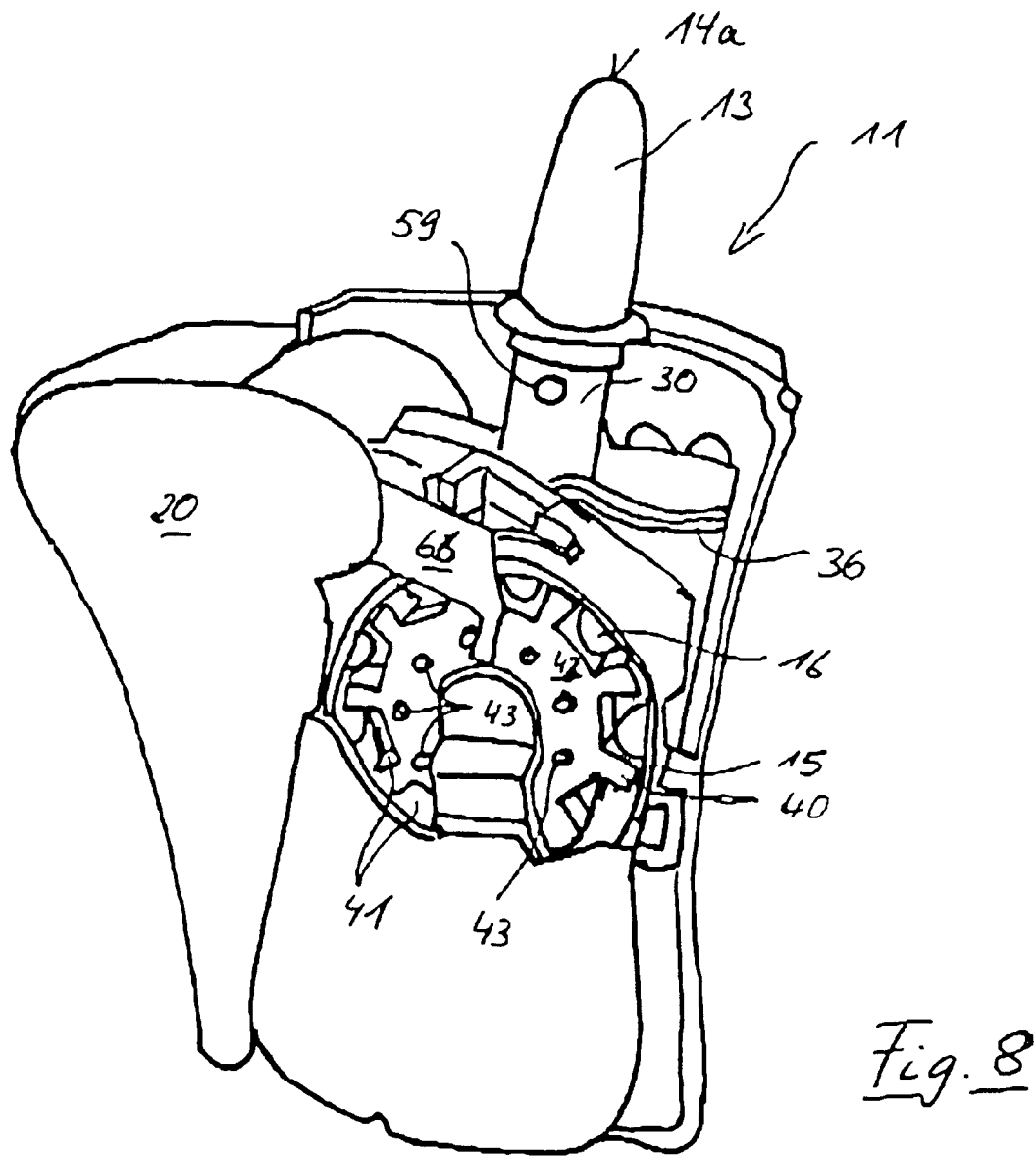

FIG. 8 A part sectional representation of a further embodiment.

In diagrammatic sectional form FIGS. 1 to 3 show a first embodiment of the invention.

The outer contour of the dispenser 11 is determined by the casing 12, the nose adaptor 13 as well as the actuating means 20, an actuating lever. The nose adaptor 13 is used for nasal active substance administration to the patient. At its front end remote from the casing 12 the nose adaptor 13 has a nozzle 14a for the escape of the medium to be discharged. On the dispenser side the discharge channel of the nose adaptor 13 issues onto the nozzle. In axially movable and correspondingly guided manner the punch 30 is placed in the casing in such a way that its nozzle-side end projects into the nose adaptor 13. On its storage chamber-side end the punch 30 is constructed in such a way that it is able to perforate or puncture the cover of the storage chamber 16. For this purpose the punch 30 e.g. has two rectangular, crosswise, conical cutting edges oriented towards the storage chamber 16. Said cutting edges are sufficiently strong and have sufficiently good cutting characteristics in order to cut through the film material used as the storage chamber cover and which can e.g. be of vacuum metallized plastic sheeting in such a way that during the separating or cutting process there is no sheet material chip formation. The prevention of chip formation is important as chips could be in a position to at least partly block the discharge channel 14 and consequently could unintentionally reduce the discharge of the given medium quantity, so that the predetermined, portionwise quantity of active substance can no longer be administered. In addition, the storage chamber is to be reliably opened at the punch perforation point. It is particularly advantageous for the perforated material to sealingly engage on the punch which has penetrated the storage chamber.

On the punch 30 is also formed the contact ring 35, which on the one hand can be used for the surface-flush engagement on the surface of the perforated cover of the storage chamber 16 and also, in conjunction with the operating slide 33 can be used for operating the punch, namely for pressing down the punch 30 in the direction of the conveying drum 40 with the receptacle 41 containing a storage chamber 16 of the blister strip 15. To ensure that in its unoperated rest position the punch does not engage with the blister strip 15, there is a leaf spring 36 fixed to the casing 12 and also fixed in a correspondingly constructed receptacle 37 and which urges the punch 30 in the direction of the nozzle 14a. The spring tension is chosen in such a way that in the inoperative state the punch 30 is securely held in its rest position shown in FIG. 1 and that the actuating forces to be applied by means of the operating slide 33 do not exceed an appropriate amount.

The storage chambers of the blister strip 15 which are not shown in FIGS. 1 to 3 are received by the receptacles 41 of the conveying drum 40 and are held in oriented manner therein, at least in the drum rotation direction. The blister strip 15 is preferably stocked in the form of a drum store 18, so that a larger blister strip length and consequently a larger number of storage chambers can be stocked. The diameter of the drum store 18, particularly the internal diameter of the wound on blister strip is limited by the material stiffness of the blister strip. The blister strip is unwound in stepwise manner from the stocked material during the sequence of operations of the dispenser and initially passed to the conveying drum 40, which is at least partly looped by the blister strip 15. The spacing between the storage chambers on the blister strip and the spacing between the receptacles 41 on the circumferential side 49 of the conveying drum 40 must be matched to one another. The area in which the conveying drum 40 is looped by the blister strip 15 extends at least over the part facing the punch 30. It is advantageous in the looping area if at least zonally guide means 28 are provided, which limit the radial clearance between the blister strip 15 and the conveying drum 40. Following the looping area the blister strip 35, which now only has emptied storage chambers, leaves the casing 12 through the discharge shaft 19. At the end of the discharge shaft 19 can be provided a sharp edge 27, so that portions of the projecting blister strip can be torn off and disposed of.

For the actuation of the dispenser 11 an actuating means 20 is provided, which is held in its unactuated rest position by the action of the return spring 25. Through actuations of the actuating means 20 the storage element 21, in the present case a spring store can be pretensioned. The spring store 21 is on the one hand supported on the actuating means 20 and on the other on a carrier plate 26. From the carrier plate 26 projects both the operating slide 33 and the slide 44, which acts on the dogs 43 of the conveying drum 40. On the carrier plate 26 is also constructed a stop pin 23, which cooperates with the stop element 24 provided on the actuating means 20, the two elements serving to limit the relative path with respect to one another.

On its circumferential side 49 the conveying drum 40 has receptacles 41 for storage means. On at least one of its end faces 42 it has dogs 43 arranged concentrically to its casing-fixed pivot pin 52. The dogs 43 are in the form of cylindrical protuberances facing the end face 42. With each receptacle 41 for a storage chamber is associated a dog 43. The dogs 43 are located on material tongues 45 constructed in the end face 42. A U-shaped slot 45a separates the material tongue 45 from the remaining surface of the end face 42. The dogs 43 are in each case located at the free end of the material tongues 45 where they are not connected with the end face 42. To ensure that there is no turning back of the conveying drum 40, on the casing side is constructed a reverse preventer 50, which cooperates with the dogs 43. On rotating or turning the conveying drum in the sense of providing the next following storage chamber at the position oriented with respect to the punch 30, it is possible to pass over the preferably ramp-like reverse preventer in that the dog, counter to the action of the material elasticity of the material tongue 45, is pressed into the plane of the end face 42 in the axial direction of the pivot pin 52. On the reverse preventer is constructed a contact face 51, which essentially has the outer contour of a dog 43 and bounds the ramp of the reverse preventer. Thus, an edge is formed on the ramp behind which the dog 43, as a result of the material elasticity of the material tongue, jumps back into its original position and then as a result of the engagement on the contact face 51 is no longer able to be turned in the opposite direction. The position of the reverse preventer 50 with respect to the position of the punch 30 must be such that if a dog 43 has just passed over the reverse preventer with its contact face 51, a receptacle 41 for a storage means 16 is precisely in the position in which it is oriented with respect to the punch 30. Preferably the reverse preventer is positioned diametrically, precisely facing the punch 30.

FIG. 1 shows the dispenser 11 in its unactuated starting position. If the dispenser is actuated by its actuating means 20, initially pretensioning takes place of the storage element 21 in the form of a spring store, which is located between the carrier plate 26 and the actuating means 20. At this time the carrier plate is held in position-fixed manner with respect to the casing 12 by a locking action with the latter. During this actuation only the spring store 21 and return spring 25 are pretensioned.

This leads to the position shown in FIG. 2, where both the return spring 25 and spring store 21 are pretensioned. The contact cam 27 constructed on the part of the actuating means 20 has almost reached the position in which it releases the locking between carrier plate 26 and casing 12. The actuating means 20 has almost reached its actuation end position. During the further movement sequence it is moved on up to its actuating end position in which then the contact cam 27 releases the locking connection between carrier plate 26 and casing 12. This procedure has the advantage that the discharge process taking place after the release of this locking connection takes place solely due to the action of the spring store 21 and consequently an action on the part of the user at this time is no longer necessary. It can be advantageous if, simultaneously with the release of the locking connection between carrier plate 26 and casing 12, a locking connection is formed between casing 12 and actuating means 20, so that the actuating means is held in the unchanged position and consequently at this time no return process of the actuating means 20 can be carried out. Thus, the actuating sequence for the discharge and conveying of the blister strip by means of the conveying drum 40 are completely independent of the sequence of the actuation of the actuating means 20. It is in particular impossible for the user to carry out only partial actuations or other inappropriate actuations. He is forced to actuate the actuating means 20 to its end position, no significance being attached to the type of actuation, because the energy stored in the spring store is independent of the sequence of actuation of the actuating means 20. Only as a result of the here intermediately stored energy is the complete discharge process performed.

From the position shown in FIG. 2 there is a passage into the position of FIG. 3 during an actuating sequence.

FIG. 3 shows the mutual positioning of the parts at the end of a discharge process before the actuating means 20 and the movable parts of the dispenser 11 have again been brought back to the starting position shown in FIG. 1.

If the contact cam 27 releases the locking connection between the carrier plate 26 and the casing 12 and simultaneously the actuating means 20 is held in the previously reached position either by the user or by locking means, there is now a relaxing of the spring in that the carrier plate 26 arranged in guided manner in the casing 12 is moved towards the conveying drum 40.

During the relaxation of the spring store 21 the carrier plate 26 with the elements fixed thereto is moved towards the conveying drum 40. Firstly the slide 44, which has an essentially beam-like construction and which is relatively movable along a circular chord with respect to the conveying drum 40, slides along the end face 42 of the conveying drum 40 with its dogs 43. In the starting position of the slide 44 shown in FIGS. 1 and 2 a dog 43 is in engagement with the lower longitudinal edge 55. Due to the fact that the dog 43 is in engagement with the slide 44, an extraction of blister strips from the casing 12 is prevented in that a rotation of the conveying drum 40 in the feed direction is prevented.

During the further translatory movement of the carrier plate 26, the end face 56 of the slide 44 engages with a dog 43. As from this time it is possible for the dog 43, along which is moved the lower longitudinal edge 55 of the slide 44, to either pass into a recess of the slide 44 or, as a result of a corresponding design of the longitudinal edge 55, beneath the slide 44. Driven by the slide 44 the drum via the dog 43, which is in engagement with the end face 56 of the slide 44, is further rotated in such a way that the next recess 46 with the storage chamber 16 of the blister strip 15 located therein is in position facing the punch 30. At this time the dog 43 has rotated on to such an extent that its upper edge, considered in the direction of the punch 30, is located below the lower edge 55 of the slide 44. The latter can consequently slide past the dog 43 and a reverse preventer effect arises in that said dog 43 is still in engagement with the lower longitudinal edge 55 of the slide 44. Simultaneously, considered counter to the rotation direction of the conveying drum, the next but one dog 43 comes into engagement with the lower longitudinal edge 55 of the slide 44, which prevents a further rotation or twisting of the drum. As both a rotation in the conveying direction of the drum and in the opposite direction is to be prevented, there is a position-secured orientation of a receptacle 41. The recess 46 and the storage chamber 16 located therein are in a fixed oriented position towards the punch 30.

Only when this position of the conveying drum 40 has been reached does the operating slide 33 with its control edge 34 come into engagement with the punch and the control edges constructed there, e.g. the contact ring 35. The construction of the control edge 34 of the operating slide 33 is such that the punch 30 initially moves in the direction of the storage chamber 16, which is held in oriented manner towards the punch 30 in the corresponding receptacle 41 of the conveying drum 40 and counter to the action of the leaf spring 36. The punch with its appropriately constructed edges then perforates the material sealing the storage chamber 16, generally a sheet or film material and which is usually metal vapour coated. For this purpose between the pump chamber 22, in which is inserted the pump piston 57 connected to the carrier plate 26, and the second flow channel 32 of the punch 30 a fluidic connection is provided, e.g. by contact between the hose end pieces. Simultaneously the punch 30 can be constructed as a slide of a slide valve, so that on reaching the end position of the punch in which the tip of the punch completely penetrates the storage chamber 16, the cover of the storage chamber 16 is perforated, but still sealingly engages in annular manner on the punch 30. The valve opens when the punch 30 has reached its end position, so that the fluid, namely air, compressed in the pump chamber 22 can escape through the flow channel 32 of the punch 30 into the storage chamber 16. There the fluid is mixed with the medium in the storage chamber 16, e.g. a liquid or powder and passes out through the first flow channel leading to the nozzle 14a. This position is shown in FIG. 3.

On ending the discharge either the locking connection between the actuating means 20 and the casing 12 is released, or the user releases the actuating means 20. As a result of the action of the return spring 25 and the leaf spring 36 the movable parts are returned to the starting position shown in FIG. 1, so that the dispenser is ready for the next actuation.

FIG. 1 shows an alternative construction of a dispenser according to the invention. Unlike in the embodiment of FIGS. 1 to 3 there is no automatic return of the actuating means 20. Instead the actuating means 20 are transferred by the user from the end position of FIG. 3 into the actuation starting position of FIG. 1. Otherwise the different elements of FIG. 4 correspond to the corresponding elements of FIGS. 1 to 3 and, if present, are given the same reference numerals.

The medium is discharged by means of the nozzle 14a into the nose adaptor 13. On its outside the punch 30 has a connecting piece for the second flow channel, which can fluidically connect the punch to the pump chamber 22. The leaf spring 36 keeps the punch 30 in its rest position and can be brought into its discharge position by the operating cam 33, which is connected to the carrier plate 26 not shown in this drawing. For this purpose during an actuation the control edge 34 of the operating slide 33 engages with the contact ring 35 on the punch.

A blister strip 15 is made available in the form of a drum store 18. The blister strip 15 has a plurality of storage chambers 16, which in each case contain medium 17.

The blister strip 15 is at least zonally guided over the conveying drum 40, which has receptacles 41 for the storage chamber 16 of the blister strip 15. On its circumferential side 49 the conveying drum is provided with receptacles 41. On the end face 42 the conveying drum 40 has dogs 43, which are constructed as fixed protuberances located on the end face and projecting axially therefrom. In the actuation starting position shown the slide 44, which is connected to the base plate 26, serves both as a reverse preventer and a preventer preventing an extraction of the blister strip from the dispenser, i.e. a twist preventer. For this purpose in the represented, unactuated starting position, the end face 56 of the slide 44 is in engagement with first dog 43. The lower longitudinal edge 55 is in engagement with a second dog 43. The contact or engagement between a dog 43 and the end face 56 prevents a turning back of the conveying drum 40. As a result of its engagement with the lower longitudinal edge 55 of the slide, the second dog 43 prevents a twisting or turning of the conveying drum. Thus, slide 44 and drum 40 prevent a complete twist barrier for said drum 40.

The operating sequence for a dispenser of the type shown in FIG. 4 entirely corresponds to the operating sequence of a dispenser in the embodiment according to FIGS. 1 to 3. Thus, in this connection reference is made to the corresponding description relative to FIGS. 1 to 3.

FIG. 5 shows in a diagrammatic sectional view the punch 30 and flow channels 31, 32 used for discharging the medium 17 from the storage chamber 16 of the blister strip 15. The blister strip 15 is on the one hand held by guide elements and on the other by correspondingly shaped recesses 46 on the circumferential side 49 of the conveying drum 40. On the end face 42 of the conveying drum 40 are constructed dogs 43 on which can act the slide 44. The slide 44 has a recess 46 into which can be introduced a dog 43. The recess 46 is constructed in such a way that it on the one hand extends along the lower longitudinal edge 55 of the slide 44 and on the other faces the end face 42 of the conveying drum 40. So that the slide 44 performs a linear movement following a circular chord of the conveying drum 40, guide rails 58 are provided for guiding the same. The guide rails 58 are constructed in the casing 12 of the dispenser 11.

In the represented actuating position of the dispenser 11 the punch 30 is immersed in the storage chamber 16 with the medium 17. The punch has perforated with its terminal edges the closure material hermetically sealing the storage chamber 16. The second flow channel for supplying fluid from the pump chamber 22 to the storage chamber 16 is connected by means of the connection point 59 to the fluid channel 60 leading from the storage chamber 22 to the connection point 59. As the storage element 21 only ensures the performance of a stroke of the pump piston 57 when said fluidic connection is produced via the connection point 59, there is no need to provide an operating valve in the fluid path between pump chamber 22 and the second flow channel 32. The situation would be different if the energy for the discharge was stored by compressing the fluid in the pump chamber before the punch 30 had penetrated the storage chamber and consequently a discharge of medium 17 from the storage chamber 16 via the flow channel 14 to the nozzle 14a and consequently to the application point was not yet possible.

The fluid displaced from the pump chamber 22 passes via the flow channel 60 and the second flow channel 32 of the punch 30 into the storage chamber 16, where it is mixed with the medium 17 kept in the storage chamber 16. It is independent of the form of the medium, namely no matter whether it is pasty, liquid or solid. As the punch 30 terminates in a virtually sealing manner in the material sealing the storage chamber, the only way out from the storage chamber 16 for the mixture of medium 17 and supplied fluid is the first flow channel 31. The first flow channel 31 leads to the discharge channel 14 in the nose adaptor 13 and consequently to the nozzle 14a, where fluid and medium are discharged from the dispenser 11.

FIG. 6 diagrammatically shows in the unactuated rest position, a detail view of the conveying drum 40 and slide 44.

On the conveying drum 40 are located dogs 43 projecting axially from material tongues 45. The material tongues 45 are formed by slots 45a made in the end face 42 of the conveying drum. The dogs 43 are positioned concentrically to the rotation axis 52 of the conveying drum 40.

It is also possible to see in the drawing the punch 30 with the contact ring 35. On the one hand the punch 30 is guided in the nose adaptor 13 and on the other is held in its unactuated rest position by the leaf spring 36. By means of the operating slide 33 with its control edge 34 the punch 30 can be moved in the direction of the conveying drum, as described hereinbefore in conjunction with the description of the operating sequences.

On actuating the dispenser the slide 44 is moved in the direction of the top, first dog 43a. As soon as the end face 56 of slide 44 engages with the dog 43a, the conveying drum performs a rotary movement about its rotation axis 52. The following, second dog 43b slides into the recess 46 constructed on the slide 44, which extends in an area of the lower longitudinal edge 55 of the slide 44 and which is oriented towards the end face 42 of the conveying drum 40. At its rear end, considered in the movement direction of the slide 44, it is possible to provide the recess 46 with a stop face 47. This stop face 47 can engage with the second dog 43b and therefore can fulfil a conveying function for continuing the rotary movement of the conveying drum 40 in the actuating direction and can also constitute a reverse preventer during dispenser actuation. The stop face 47 is plane-parallel to the end face 56 of the slide 44, so that the second dog 43b is not in a position to pass over the stop face 47. The movement path of the conveying drum and the slide 44 in the conveying direction is limited in that the one from next dog 43c with respect to the first dog 43a engages with the lower longitudinal edge 55 of the slide 44. Through the engagement of the dog 43b on the stop face 47 and the simultaneous engagement of the dog 43c on the lower longitudinal edge 55, it is possible to produce a clearly defined position of the conveying drum 40, which is twist-secured in both rotation directions of the conveying drum 40.

To enable the slide 44 to be moved back into its starting position without turning the conveying drum 40, it is advantageous to provide a further reverse preventer acting on the conveying drum 40 in preferred manner by means of dogs 43 and as has e.g. been described in conjunction with FIGS. 1 to 3. It is also advantageous if the side 48 of the recess 46 facing the stop face 47 also has a ramp-like construction. On moving back the slide 44 the opposite side 48 can press the dog 43b in the direction of the end face 42 of the conveying drum 40. This takes place counter to the action of the forces produced as a result of elastic deformation by the material tongue 45b of the dog 43b. As a result the slide 44 can slide over the dog 43b during the rearward movement.

FIGS. 7a to 7c show an alternative embodiment of a punch 30, where in FIGS. 7a and 7b is shown the positioning of the punch in the nose adaptor and the construction of the connection point 50 of the flow channel 60.

The punch housing incorporates an annular body and a connection point 59 in order to bring about a fluidic connection of the annular body to the pump chamber 22. A fluid flow then passes through the connection point into the second, annular flow channel 32 and flows, considered radially on the outside of the storage chamber 16 of the blister strip 15, into said storage chamber. As the external diameter of the punch 30 is adapted to the internal diameter of the blister strip storage chamber, it is possible to ensure a flow along the housing wall of the storage chamber 16. For perforating the cover terminating the storage chamber 16, the punch 30 has two rectangular, crossing cutting edges 62. The cutting edges can in particular have a substantially triangular cross-section and ensure that after cutting through the cover it is possible to introduce the punch into the storage chamber 16. The sealing engagement of the punch on the outside of the storage chamber 16 can be ensured by the side wall of said punch 30 constructed as a stop ring 35.

The air flowing concentrically on the edge of the storage chamber 16 escapes via the first flow channel 31, which is arranged concentrically and centrally with respect to the second flow channel 32. Use is made of the deflection effect which arises when the inflowing air, flowing in from all sides, meets at the lowest point of the container and then can only escape upwards in the centre. This ensures a good discharge of the medium 17 to be discharged from the storage chamber 16. FIG. 7 is a view from below of the punch 30 in which the discharge channel 31 leads to the discharge channel 14, which issues into the discharge opening 14a.

On its outside the punch 30 also has an overflow hole 61, which is fluidically connected to the atmosphere. The overflow hole is fluidically connected to the second flow channel 32 and a check valve ensures that no fluid escapes from the pump chamber 22 via the overflow hole 61. As a result of the overflow hole 61 the user can assist the discharge process by actively sucking in air. So that said active suction is assisted, it must be possible that the air subsequently flowing through the overflow hole 61 and which essentially corresponds to the sucked in volume of the user can take part in the discharge process. It can also be provided that the overflow hole 61 is connected to the first flow channel 31 and the additional suction is solely brought about by the Venturi effect of the additional air flow. As a result of the high flow rate of the large volume flow through the overflow hole 61, medium to be discharged or a mixture of fluid and medium is sucked out of the storage chamber 16.

FIG. 7c is a perspective view of partial elements of the punch 30. The air flowing in via the connection point 59 in the interior of the housing of the punch 30 reaches the annular section 63 and between the sleeve 64 and needle 65, which forms the punch with the cutting edges 62 and which also has a sleeve-like body, has the first flow channel 31 in its interior. The second partial view of FIG. 7c shows the needle 65 located in the interior of the sleeve 64 and in which is formed the first flow channel 31 used for discharging the medium. In addition, on the needle 65 are provided the cutting edges 62 for cutting the storage container cover.

FIG. 8 shows an alternative design of a dispenser.

The medium is discharged by means of the nozzle 14a in the nose adaptor 13. The punch 30 is located in the interior of the housing and is fluidically connected to the discharge channel 14 of the nose adaptor 13. On its outside the punch 30 has a connection point 59 by means of which the punch is fluidically connectable to the pump chamber 32. By means of leaf springs 36 the punch 30 is held in its inoperative position. For guiding the linear movement guide cams 66 are constructed in the interior of the housing 12 of dispenser 11. By a not shown switching means, e.g. a slide valve, the punch 30 can be brought from the inoperative position into the represented operating end position.

The blister strip 15 having a plurality of storage chambers 16 is made available in the form of a drum store 18. The blister strip 19 is at least zonally guided over the conveying drum 40, which has receptacles for in each case one storage chamber 16 of the blister strip 15. For this purpose the conveying drum is provided on its circumferential side 29 with receptacles 41. On the end face 42 the conveying drum 40 has dogs 43, which are constructed as axially projecting protuberances. The hook claw 66 engages behind one of the dogs 43 on moving out the actuating means 20 and turns the conveying drum 40 during this tensioning movement by precisely one storage chamber 16 or precisely one receptacle 41. During the actuation of the actuating means 20 the return stroke of the hook claw 66 is guided in such a way that with its element engaging behind the dog 43 the hook claw 66 is led past the dogs 43 in axially displaced manner, so that there is no backward rotation of the conveying drum. There can also be corresponding locking means for maintaining the position of the conveying drum 40.

The operating sequence for the actuation of a dispenser according to FIG. 8 completely corresponds to the actuating sequence of a dispenser according to FIGS. 1 to 3 and in this connection reference should be made to the corresponding description.

As a result of the dispenser according to the invention media of different types can be discharged from a dispenser. It is possible to discharge pulverulent, liquid or pasty media. Generally ambient air is used as the fluid, which is displaced from the pump chamber 22 and which ensures the discharge of the medium from the storage chamber. However, other fluids can also be used. The invention has also been illustrated by application to a dispenser for the nose. However, other applicators can be used in place of the nose adaptor 13. An example of another applicator is a throat adaptor. Thus, the dispenser according to the invention has numerous uses. This is particularly the case with media containing active pharmaceutical substances, e.g. analgesics or anti-migraine agents or other medicaments which are more particularly administrable via the nose. The use of the dispenser is not limited to the pharmaceutical or medical sector.

What is claimed is:

1. Dispenser for discharging media, said dispenser having storage means for containing at least one active pharmaceutical substance in portions in respective storage chambers of said storage means and said dispenser having a punch which can be introduced into the storage chambers, and wherein an actuating means is provided for both positioning of a storage chamber relative to the punch and for discharge of the medium, and wherein the storage means includes a blister strip having a plurality of storage chambers with dischargeable medium, in which the blister strip is made available in a drum store.

2. Dispenser according to claim 1, wherein through the actuation of the actuating means firstly the next, filled storage chamber is made available, followed by the discharge of the medium therefrom.

3. Dispenser according to claim 1, wherein the medium is discharged by pretensioning a storage element during a first actuating phase and relaxing the storage element during a second actuating phase.

4. Dispenser according to claim 3, wherein the storage element is a pump chamber and a pressure is built up in the pump chamber during the first actuating phase, the pump chamber being closed by an operable valve and during the transition from the first to the second actuating phase the valve is actuated in the opening sense, as a function of the actuating path of the actuating means.

5. Dispenser according to claim 1, wherein the medium is discharged by blowing out the fluid contained in the pump chamber.

6. Dispenser according to claim 1, wherein on the punch is formed at least one first flow channel for discharging the medium from the storage means and a second flow channel for the supply of the fluid from the pump chamber into the storage chamber.

7. Dispenser according to claim 6, wherein the punch is constructed as an operating element for the valve sealing the pump chamber.

8. Dispenser according to claim 6, wherein the second flow channel has an annular construction and surrounds the first flow channel.

9. Dispenser according to claim 6, wherein the punch is constructed in such a way that the edge of the punch engages in sealing manner on perforating material.

10. Dispenser comprising:
   a conveying drum for conveying and orienting means for storage, in which the circumferential surface of the conveying drum carries receptacles for in each case one storage chamber; and
   wherein the means for storage includes a blister strip having a plurality of storage chambers with dischargeable medium, the blister strip being made available in a drum store.

11. Dispenser according to claim 10 wherein a reverse preventer acting on the conveying drum is provided, which allows a rotary movement of the conveying drum in a conveying direction and prevents a rotary movement counter to the conveying direction and the reverse preventer intervenes in an empty receptacle.

12. Dispenser according to claim 10, wherein on an end face, the conveying drum has dogs and preferably a dog is endwise associated with each receptacle of the circumferential surface.

13. Dispenser according to claim 12, wherein the actuating means has at least one slide acting on the dogs, the slide being at least constructed either as a twist preventer or as a reverse preventer.

14. Dispenser according to claim 13, wherein the slide, by means of the actuating means, can be slid and guided in such a way that along a circular chord along the end face is moved past the conveying drum.

15. Dispenser according to claim 12, wherein the dogs are constructed as cylindrical protuberances projecting axially from the end face and positioned concentrically to the rotation axis of the conveying drum.

16. Dispenser according to claim 15, wherein the dogs are located on material tongues formed in the end face, the material tongues preferably being U-shaped, being connected by a material web in the rotation direction of the conveying drum and being constructed in such a way that they can be brought by the height of the particular protuberance and counter to the resulting bending forces in the direction of the interior of the conveying drum.

17. Dispenser according to claim 12, wherein the actuating means has a hook claw and is in engagement with at least one dog for conveying the conveying drum and during the return movement is moved back past at least one dog in axially displaced manner.

18. Dispenser comprising:

a conveying drum for conveying and orienting means for storage, in which the circumferential surface of the conveying drum carries receptacles for in each case one storage chamber;

wherein on an end face, the conveying drum has dogs and preferably a dog is endwise associated with each receptacle of the circumferential surface;

wherein the actuating means has at least one slide acting on the dogs, the slide being at least constructed either as a twist preventer or as a reverse preventer;

wherein the slide, by means of the actuating means, can be slid and guided in such a way that along a circular chord along the end face it is moved past the conveying drum; and wherein the slide has a substantially beam-like construction and its longitudinal edge extends in the direction of the circular chord along which the slide can be moved with respect to the conveying drum, its end face being oriented towards a dog and during an actuating process the end face of the slide engages with a dog, that the slide has a recess constructed on its side facing the end face of the conveying drum and which extends in the area of the longitudinal edge facing the dogs, the recess serving to receive the dog following the dog which engages with the end face of the slide during an actuation, that the rear stop face in the movement direction, which is oriented parallel to the end face of the slide and which bounds the recess is so oriented in position with respect to the end face and dogs that a non-positive connection directed towards the conveying direction of the conveying drum can be produced between a dog located in the receptacle and the stop face and that on the front side, which bounds the recess and faces the stop face, the recess has a ramp-like construction.

19. Dispenser comprising:

a conveying drum for conveying and orienting means for storage, in which the circumferential surface of the conveying drum carries receptacles for in each case one storage chamber; and a reverse preventer acting on the conveying drum and diametrically facing the slide and wherein a blocking action is achieved by frictional connection between a conveying drum-side dog and a casing-fixed contact face, over which it is possible to pass in the conveying direction of the conveying drum.

20. Dispenser according to claim 10, wherein the dispenser serves to discharge dischargeable media packed portions in the respective storage chambers and containing at least one pharmaceutical substance, and said dispenser having a punch, which can be introduced into the storage chamber.

* * * * *